United States Patent
Strauss

(10) Patent No.: US 8,745,806 B2
(45) Date of Patent: Jun. 10, 2014

(54) PEN STYLE TOOL AND KIT FOR CLEANING VALIDATION

(75) Inventor: Michael Strauss, Tamarac, FL (US)

(73) Assignee: Foamtec International Co., Ltd., Oceanside, CA (US)

( * ) Notice: Subject to any disclaimer, the term of this patent is extended or adjusted under 35 U.S.C. 154(b) by 408 days.

(21) Appl. No.: 13/004,749

(22) Filed: Jan. 11, 2011

(65) Prior Publication Data

US 2011/0296639 A1 Dec. 8, 2011

Related U.S. Application Data

(60) Provisional application No. 61/351,236, filed on Jun. 3, 2010.

(51) Int. Cl.
*A46B 7/04* (2006.01)

(52) U.S. Cl.
USPC ............................. 15/176.1; 15/159.1; 15/171

(58) Field of Classification Search
USPC ...................................... 15/159.1, 171, 176.1
See application file for complete search history.

(56) References Cited

U.S. PATENT DOCUMENTS

| | | | | |
|---|---|---|---|---|
| 4,854,761 A * | 8/1989 | Smith et al. | ................... | 401/196 |
| 5,299,341 A * | 4/1994 | Wakao | ......................... | 15/210.1 |
| 6,551,265 B1 * | 4/2003 | Miguel | .............................. | 604/1 |
| 7,287,295 B2 * | 10/2007 | Treacy et al. | ................. | 15/210.1 |
| 2007/0137319 A1 * | 6/2007 | Nacson et al. | ................... | 73/864 |
| 2007/0186365 A1 * | 8/2007 | Armaly | ........................ | 15/244.1 |

OTHER PUBLICATIONS

Notification of Transmittal of the International Search Report and the Written Opinion of the International Searching Authority, or the Declaration in International Application No. PCT/US2011/037514 with a mailing date of Sep. 2, 2011.

* cited by examiner

*Primary Examiner* — Lee D Wilson
*Assistant Examiner* — Shantese McDonald
(74) *Attorney, Agent, or Firm* — Zeman-Mullen & Ford, LLP

(57) ABSTRACT

A tool and kit for cleaning and/or cleaning validation which includes a handle, a tip, and an ejection mechanism connected to the handle that is capable of ejecting a cleaning element (such as a swab, brush, or applicator) from the handle without the need for a user to handle the cleaning element. The cleaning element is seated on the tip and can be ejected from the handle either with or without the tip on which it is seated.

17 Claims, 3 Drawing Sheets

PEN STYLE TOOL AND KIT FOR CLEANING VALIDATION

CROSS-REFERENCE TO RELATED APPLICATIONS

This application claims the benefit of, and priority to U.S. Provisional Application No. 61/351,236, filed Jun. 3, 2010, which application is hereby incorporated by reference in its entirety.

FIELD OF INVENTION

The present invention is directed to a pen style tool and kit for cleaning validation where the effectiveness of cleaning protocols and procedures needs to be measured or determined after the cleaning of equipment that is used in the manufacture of products such as pharmaceuticals, medical devices, and any other product where contamination during manufacture may be an issue. In addition, the tool and kit of the present invention may be used in any application where a swab, applicator, brush, etc., is used such as, for example, in drug delivery systems, arts and crafts, cosmetics, forensics, environmental monitoring, podiatry, dentistry, and detailing. This list of potential applications is not intended to be exclusive as the tool and kit of the present invention may be used in any number of additional applications.

The tool of the present invention includes a handle having an ejection mechanism and a tip where a swab, applicator, brush, or other similar type of cleaning element positioned on the tip can be ejected from the handle. The tip and handle may comprise separate elements or, alternatively, they may comprise one continuous element where the swab, brush, or applicator is capable of being ejected from the tip. The ejector mechanism is contained within, and/or connected to, the handle such that a tip containing a swab, applicator, brush, etc., may be ejected from the handle. Alternatively, the ejector mechanism may be configured to eject a swab, brush, or applicator from the tip.

BACKGROUND OF THE INVENTION

Swabs are typically used to determine the effectiveness of cleaning protocols used for cleaning manufacturing equipment such as the manufacturing equipment used in making pharmaceuticals and other products where it is important to eliminate contaminants during manufacture. Analysis of total organic carbons, or organic contaminants, is an example of one method used to validate cleaning protocols and processes. High performance liquid chromotagraphy (HPLC) and ultraviolet (UV)/visible spectroscopy are other examples of analytic methods used to validate cleaning protocols and procedures. Traditionally, polyester swabs are used for surface sampling and cleaning validation work.

A prior art swab and handle are shown in FIG. 1. Prior art polyester swabs 10 are positioned on a swab handle 12 that comprises a head paddle 14 (for supporting a swab) at the end of a long rigid handle 16. The swab handle 16 includes notches 18 so that the head 14 containing the swab 10 can be easily snapped off or cut off for convenient sample handling. Prior art swabs and handles may be used for cleaning certain areas as well as for determining the effectiveness of cleaning protocols and procedures.

Traditional prior art swabs and handles where the heads are cut or snapped off by the operator to analyze the swab for contaminants introduce the potential for contamination of the samples and the potential for giving a false positive test result. The operators and cutting devices of traditional prior art swabs and handles can carry contaminants and also cause retesting problems when they are in contact with the swab head or the handle close to the swab.

Accordingly, there is a need for a tool that reduces the potential for introducing contaminants when testing samples obtained with swabs.

SUMMARY OF THE PRESENT INVENTION

The present invention is directed to a tool and kit for cleaning and/or cleaning validation. The tool may also be used for various applications. The tool includes a handle, a tip, and an ejection mechanism capable of ejecting a swab, brush, applicator, or any other type of cleaning element from the handle without the need for a user to handle the swab, brush, or applicator.

The handle and the tip may comprise two separate elements or one continuous element. In one exemplary embodiment, the handle and the tip comprise separate elements and the ejection mechanism may be contained within and/or connected to the handle such that the tip containing a swab, brush or applicator positioned on the tip can be ejected from the handle without a user touching or handling the tip or the swab, brush, or applicator. In addition, a tip containing a swab, brush, or other applicator already positioned on the tip may be loaded onto, or connected to, the handle without the need for a user to touch the tip or the swab, brush, or applicator. The ability of the swab, brush, or applicator to be removed from the handle without close handling of a user eliminates cross contamination that might otherwise be introduced. In addition, the handle may be reused many times thereby reducing waste. To reuse, a new tip containing a new swab, brush, or other applicator already positioned on the tip is loaded onto, or connected to, the handle.

In another exemplary embodiment, the handle and tip may comprise one continuous element or two separate elements and a cleaning element such as a swab, brush or applicator is positioned on the tip and the cleaning element is ejected from the tip (instead of the tip along with the cleaning element such as the swab, brush or applicator being ejected from the handle). The ejector mechanism may be contained within and/or connected to the handle such that the cleaning element (such as a swab, brush or applicator) positioned on the tip can be ejected from the tip without a user touching or handling the tip or the cleaning element (such as the swab, brush, or applicator). In addition, the cleaning element (such as a swab, brush, or other applicator) may be loaded onto the tip without the need for a user to touch the tip or the cleaning element (such as the swab, brush, or applicator). In this embodiment, the handle and tip may be reused many times thereby reducing waste.

The present invention is also directed to a kit which includes a tool comprising a handle having an ejection mechanism and a plurality of tips each containing a swab, brush, or other applicator positioned thereon. The present invention is also directed to a kit which includes a tool comprising a handle, a tip, and an ejection mechanism, and a plurality of swabs, brushes, or other applicators that can be loaded onto the tip of the tool.

BRIEF DESCRIPTION OF THE DRAWINGS

The subject invention will hereinafter be described in conjunction with the appended drawing figures, wherein like numerals denote like elements.

DESCRIPTION OF THE EXEMPLARY EMBODIMENTS

Figure 1:
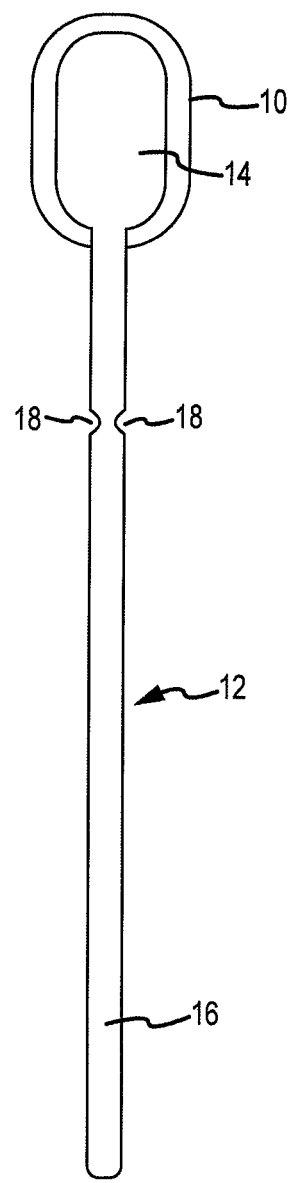
FIG. 1 is a top plan view of a prior art cleaning swab and handle used in environments where it is important to eliminate contaminants during the manufacture of products.
Figure 2:
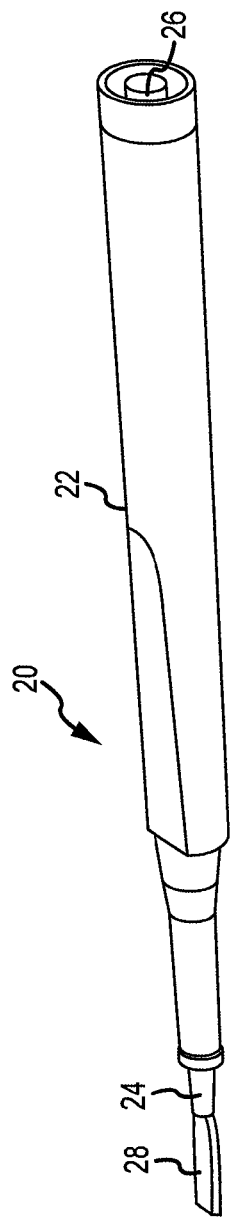
FIG. 2 is a perspective view of the cleaning tool and/or cleaning validation tool of the present invention showing the tip of the handle without the cleaning element seated thereon.

One exemplary embodiment of the tool of the present invention is shown in FIG. 2. Tool 20 includes a handle 22, a tip 24, and an ejection mechanism (not shown but contained within the interior of handle 22). Handle 22 includes a button type element 26 which is engaged with the ejection mechanism such that pressing button type element 26 will cause tip 24 to eject from handle 22. Tip 24 may include a flat portion 28 on which a swab, brush, or other applicator is positioned and retained. The handle may be made from polypropylene or any other type of durable plastic material. The handle may also be made from other durable materials including, but not limited to, metals, ceramics, fiberglass, etc. In addition, the handle may be made such that it can be repeatedly sterilized, if necessary, such as by being autoclaved. The handle 22 may have two flattened sides which orient with the swab head to enable any operator to line up and attach the tip containing the swab to the handle. Orientation and attachment may be further facilitated by ensuring that the tips can only be inserted one way into the handle by aligning a triangle on the tip to the handle. The eject mechanism is protected by extending the plastic on the handle so that the swab head cannot be released unless intended. It will be understood by those in the art that any number of configurations or elements may be used to activate the ejection mechanism contained within the handle 22 in order to eject tip 24 from handle 22.

Figure 3:
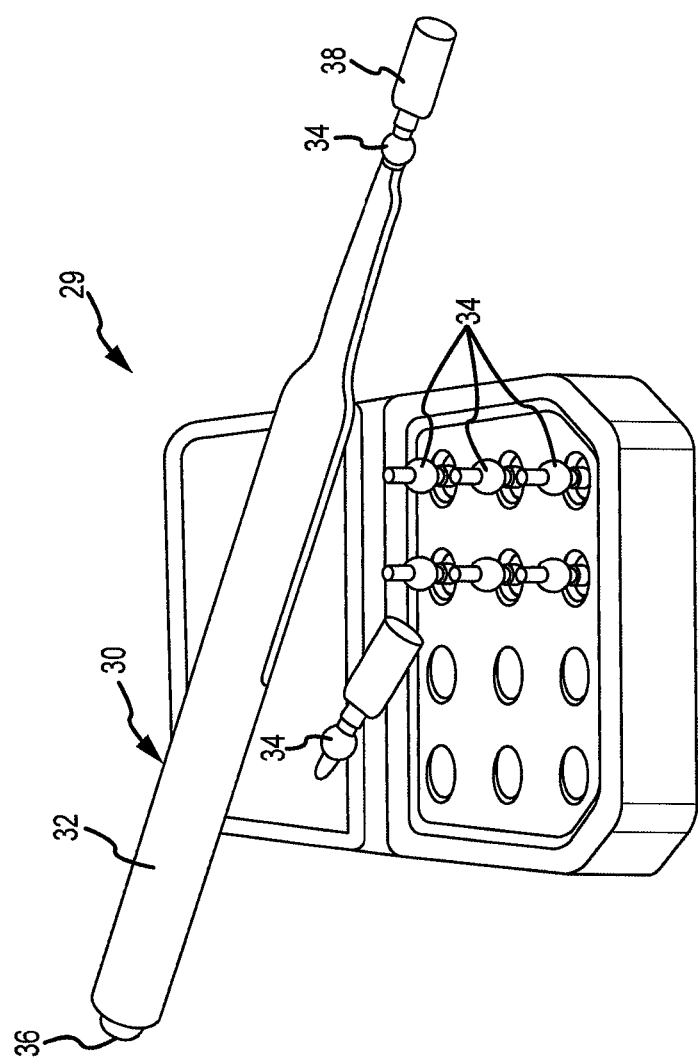
FIG. 3 is a perspective view of a kit of the present invention for cleaning and/or cleaning validation which includes the cleaning tool/cleaning validation tool of the present invention shown with a cleaning element seated on the tip of the handle of the tool and a container containing a plurality of cleaning elements each contained on a separate tip that fits onto an end of the handle.

FIG. 3 shows a kit 29 of the present invention which includes tool 30 having handle 32, tip 34 having a swab 38 positioned thereon, an ejection mechanism (not shown but contained within the interior of handle 32), and a plurality of tip members 34 which may or may not each have a swab or other applicator loaded thereon. Handle 32 includes a button 36 which is engaged with the ejection mechanism such that pressing button 36 will cause tip 34 containing swab 38 to eject from handle 32.

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

The invention claimed is:

1. A tool for at least one of cleaning and cleaning validation comprising:
a handle having at least one flattened side and an ejection mechanism;
a removable tip connected to the handle and capable of being ejected from the handle by the ejection mechanism wherein the removable tip comprises a flat portion with one or more edges such that the flat portion can be aligned with said at least one flattened side of the handle when connecting the removable tip to the handle, and a cleaning element retained on the flat portion such that it covers at least one of the one, or more edges of the removable tip.

2. The tool of claim 1 wherein the handle comprises a generally cylindrical shape with the exception of said at least one flattened side of the handle.

3. The tool of claim 1 wherein the handle includes a button type element connected to the ejection mechanism such that the button type element can be depressed to eject the removable tip from the handle.

4. The tool of claim 1 further comprising a cleaning element attached to the removable tip wherein the cleaning element comprises at least one of a swab, a brush, and an applicator.

5. A kit for at least one of cleaning and cleaning validation comprising:
a handle having at least one flattened side and an ejection mechanism; and
a plurality of removable tips each having a flat portion with one or more edges such that the flat portion can be aligned with said at least one flattened side of the handle when connecting the removable tip to the handle, and a cleaning element seated on the flat portion such that it covers at least one of the one or more edges of the removable tip wherein each removable tip is capable of being attached to, and ejected from, an end of the handle.

6. The kit of claim 5 wherein the handle comprises a generally cylindrical shape with the exception of said at least one flattened side of the handle.

7. The kit of claim 5 wherein the handle includes a button type element connected to the ejection mechanism such that the button type element can be depressed to eject the removable tip from the handle.

8. The kit of claim 5 wherein the cleaning element comprises at least one of a swab, a brush, and an applicator.

9. A kit for at least one of cleaning and cleaning validation comprising:
a handle having at least one flattened side and an ejection mechanism;
a tip connected to one end of the handle wherein the tip comprises a flat portion with one or more edges such that the flat portion can be aligned with said at least one flattened side of the handle when connecting the tip to the handle; and a plurality of removable cleaning elements each capable of being seated on the flat portion of the tip such that the cleaning element covers at least one of the one or more edges of the tip, wherein the cleaning element can be ejected from the tip with the ejection mechanism.

10. The kit of claim 9 wherein the handle comprises a generally cylindrical shape with the exception of said at least one flattened side of the handle.

11. The kit of claim 9 wherein the handle includes a button type element connected to the ejection mechanism such that the button type element can be depressed to eject the removable cleaning element from the tip.

12. The kit of claim 9 wherein the cleaning element comprises at least one of a swab, a brush, and an applicator.

13. A tool for at least one of cleaning and cleaning validation comprising:

a handle having at least one flattened side and an ejection mechanism;

a tip connected to one end of the handle wherein the tip comprises a flat portion such that the flat portion can be aligned with the flattened side of the handle when connecting the tip to the handle; and a removable cleaning element seated on the flat portion of the tip.

14. The tool of claim 13 wherein the handle comprises two flattened sides.

15. The tool of claim 14 wherein the tip comprises two flat portions such that the two flat portions of the tip can be aligned with the two flattened sides of the handle when connecting the tip to the handle.

16. The tool of claim 13 wherein the handle includes a button type element connected to the ejection mechanism such that the button type element can be depressed to eject the removable cleaning element from the tip.

17. The tool of claim 13 wherein the cleaning element comprises at least one of a swab, a brush, and an applicator.

* * * * *